United States Patent
Yu et al.

(10) Patent No.: US 11,638,579 B2
(45) Date of Patent: May 2, 2023

(54) THREE-DIMENSIONAL ATRIAL SEPTAL PUNCTURE METHOD

(71) Applicant: WUHAN LVDONG MEDICAL TECHNOLOGY CO., LTD., Wuhan (CN)

(72) Inventors: Ronghui Yu, Beijing (CN); Changsheng Ma, Beijing (CN)

(73) Assignee: WUHAN LVDONG MEDICAL TECHNOLOGY CO., LTD., Wuhan (CN)

( * ) Notice: Subject to any disclaimer, the term of this patent is extended or adjusted under 35 U.S.C. 154(b) by 652 days.

(21) Appl. No.: 16/629,035

(22) PCT Filed: Apr. 11, 2018

(86) PCT No.: PCT/CN2018/082718
§ 371 (c)(1),
(2) Date: Jan. 7, 2020

(87) PCT Pub. No.: WO2019/015361
PCT Pub. Date: Jan. 24, 2019

(65) Prior Publication Data
US 2021/0212675 A1      Jul. 15, 2021

(30) Foreign Application Priority Data

Jul. 19, 2017 (CN) .......................... 201710592492.1
Nov. 3, 2017 (CN) .......................... 201711067661.6

(51) Int. Cl.
*A61B 34/30* (2016.01)
*A61B 17/00* (2006.01)
(Continued)

(52) U.S. Cl.
CPC .... *A61B 17/00234* (2013.01); *A61B 17/3478* (2013.01); *A61B 34/20* (2016.02);
(Continued)

(58) Field of Classification Search
CPC ......... A61B 34/20; A61B 34/30; A61B 17/00; A61B 17/34; A61B 17/00234;
(Continued)

(56) References Cited

U.S. PATENT DOCUMENTS

| 5,115,814 A * | 5/1992 | Griffith ................ G10K 11/357 600/463 |
| 2008/0082136 A1* | 4/2008 | Gaudiani ............... A61B 6/481 607/9 |
| 2016/0073960 A1* | 3/2016 | Jung ..................... A61B 5/6858 600/374 |

* cited by examiner

*Primary Examiner* — Vi X Nguyen

(57) ABSTRACT

The invention discloses a three-dimensional atrial septal puncture method including positioning the heart from a body surface by a three-dimensional projection positioning method and displaying interventional instruments by the three-dimensional system and guiding the same into a heart cavity. The method also includes constructing a right atrium three-dimensional model by delivering a catheter with a positioning device to the right atrium and reconstructing and fusing pre-operative image data by the three-dimensional system. The method also includes setting parameters, connecting an interventional operating device with a pressure sensor tail wire and an electrode tail wire, and displaying a guidewire or a puncture needle. The method includes delivering and positioning the long sheath, analyzing and marking the fossa ovalis position by a structure and potential method. The method also includes analyzing the pressure difference between the left atrium and the right atrium, and judging whether the puncture is successful.

14 Claims, 7 Drawing Sheets

(51) Int. Cl.
*A61B 34/20* (2016.01)
*A61B 90/00* (2016.01)
*G16H 20/40* (2018.01)
*A61B 17/34* (2006.01)

(52) U.S. Cl.
CPC ............. *A61B 90/37* (2016.02); *G16H 20/40* (2018.01); *A61B 2017/00247* (2013.01); *A61B 2017/00292* (2013.01); *A61B 2090/064* (2016.02); *A61B 2090/367* (2016.02)

(58) Field of Classification Search
CPC . A61B 17/3478; A61B 19/201; A61B 19/203; A61B 19/5244; A61B 2017/00247; A61B 2017/00292
See application file for complete search history.

Positioning the heart from a body surface by a three-dimensional projection positioning method, displaying an interventional instrument in a three-dimensional system and guiding the same into a cardiac chamber; constructing a right atrium three-dimensional model by delivering a catheter with a positioning device to the right atrium Setting parameters of the three-dimensional system, connecting a puncture operation device with a corresponding electrode tail wire and to the three-dimensional system, and displaying a guide wire or a puncture needle in the three-dimensional system in real time Delivering a long sheath into the superior vena cava, and positioning the long sheath by using the three-dimensional system Performing the atrial septal puncture at an atrial septal marker site by the delivered atrial septal puncture needle under the guidance of the three-dimensional system Connecting a tail end of the puncture needle with a pressure sensor tail wire, and judging whether the puncture is successful by analyzing the pressure difference between the left atrium and the right atrium Sequentially delivering the guidewire and the long sheath into the left atrium after a successful atrial septal puncture

Fig. 1

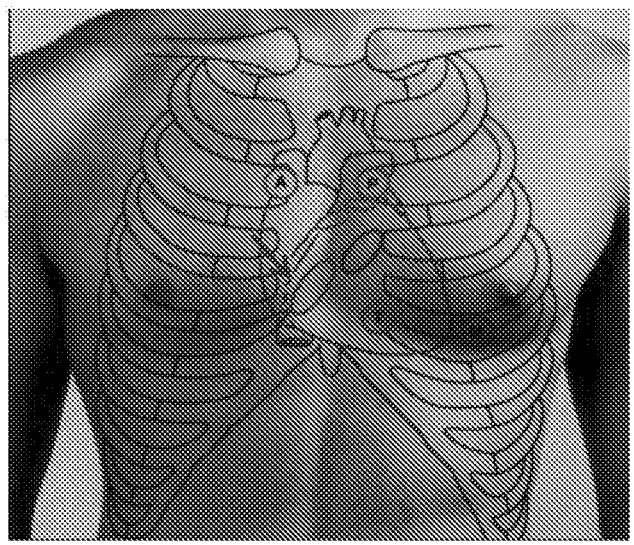

Fig. 2a

THREE-DIMENSIONAL ATRIAL SEPTAL PUNCTURE METHOD

RELATED APPLICATIONS

This application is a United States National Stage Application filed under 35 U.S.C 371 of PCT Patent Application Serial No. PCT/CN2018/082718, filed Apr. 11, 2018, which claims Chinese Patent Application Serial No. CN 201710592492.1, filed Jul. 19, 2017 and Chinese Patent Application Serial No. CN 201711067661.6, filed Nov. 3, 2017, the disclosure of all of which are hereby incorporated by reference in their entirety.

TECHNICAL FIELD

The present invention relates to a three-dimensional atrial septal puncture method which can be performed without ray and ultrasound.

BACKGROUND ART

More than 10,000,000 patients suffer from atrial fibrillation (AF) in China. Radiofrequency ablation under the guidance of a three-dimensional system is the first choice for radically treating AF. More than 400,000 cases are completed in 2016 nationwide, and the treatment amount is rapidly increasing every year. One of the important steps for completing this operation is atrial septal puncture; in addition, the atrial septal puncture is required for a variety of cardiac interventional treatment means, for example, mitral valvuloplasty, left atrial appendage occlusion, cryoablation, and radiofrequency ablation for left accessory pathways, left atrial tachycardia and atrial flutter, left premature ventricular contraction and ventricular tachycardia. At present, the mainstream atrial septal puncture in China is still the atrial septal puncture under the guidance of X-ray fluoroscopy, which is a two-dimensional plane view technology developed more than half a century ago, lacks an accurate indication given by a three-dimensional space, and takes long-time clinical accumulation to master the technology. If the heart of a patient is abnormal, the puncture difficulty is extremely high; and the success rate and safety of puncture are more influenced when the patient is too obese and the definition of an X-ray machine is not high. An atrial septal puncture guided by Intracardiac Echocardiography (ICE) advocated by foreign countries such as the United States is to add an ICE catheter on the basis of X-ray fluoroscopy. Although the visualization of the ultrasound field of view has been increased, it is still based on two-dimensional planar technology, which is difficult to reflect the true three-dimensional feeling of the heart. Because of the need of corresponding cardiac ultrasound knowledge and expensive ultrasound catheter, the equipment and technical threshold have been greatly increased. In addition, the current ICE is still limited in accuracy, which is still difficult to achieve complete accuracy for the analysis of the fossa ovalis.

In recent years, zero- or very low-radiation green electrophysiological radiofrequency ablation, which relies on three-dimensional technology, has become more and more accepted by clinical operators. Although the technology is more and more mature, zero-radiation atrial septal puncture, as a key component, has not yet been tackled.

Accordingly, there is a need for a novel three-dimensional atrial septal puncture method that can be performed with reduced or no need for x-rays and without the need for intracardiac ultrasound guidance.

SUMMARY OF THE INVENTION

The invention provides a three-dimensional atrial septal puncture method, comprising the steps of:

positioning the heart from a body surface by a three-dimensional projection positioning method, displaying an interventional instrument in the three-dimensional system and guiding the same into a cardiac chamber;

constructing a right atrium three-dimensional model by delivering a catheter with a positioning device to the right atrium;

reconstructing and fusing pre-operative image data by the three-dimensional system;

mainly analyze a right atrial septal side, and marking an atrial septal puncture site by the structure and potential analysis;

setting parameters of the three-dimensional system, respectively connecting a puncture operation device with a pressure sensor tail wire and an electrode tail wire, connecting the same to the three-dimensional system, and displaying a guidewire or a puncture needle in the three-dimensional system in real time;

delivering a long sheath into the superior vena cava, and positioning the long sheath by using the three-dimensional system;

performing an atrial septal puncture by the delivered atrial septal puncture needle under the guidance of the three-dimensional system;

analyzing the pressure difference between the left atrium and the right atrium, and judging whether the puncture is successful; and sequentially delivering the guidewire and the long sheath into the left atrium after a successful atrial septal puncture.

Preferably, the image fusion analysis is performed after the reconstruction of the three-dimensional system.

Preferably, according to an embodiment of the present invention, after the reconstruction of the three-dimensional system, the fossa ovalis is positioned by potential mapping to mark an atrial septal puncture point.

Preferably, when the atrial septal puncture point is marked, the coronary sinus is marked at a distal end by using a catheter with a pressure sensor.

The atrial septal puncture point located in the fossa ovalis is at a height level of the His bundle in the longitudinal section, not more than 5 mm above or below the level, and is located in a bulge region at a position of last two fifths to one quarter of the septum in the transverse section.

A guidewire or an atrial septal puncture needle is defined as a mapping catheter, and the mapping catheter is connected into the three-dimensional system by connecting a tail wire.

The long sheath is delivered into the superior vena cava by using a catheter with a magnetic positioning device and then exchanged into an inner sheath with a guidewire; the guidewire always remains outside the inner sheath. The length of the distal end of the guidewire extending out of the inner sheath is not greater than 1-2 mm, so that the head end of the guidewire can be displayed in the three-dimensional system.

The distal end of the guidewire is delivered into the superior vena cava directly by means of slight or even no exposure to the sheath; the right atrial septal face is displayed at a left anterior oblique angle of 45 degrees and a left anterior oblique angle of 135 degrees respectively in the three-dimensional system; the guidewire is exchanged into the atrial septal puncture needle, the relative positions of the atrial septal puncture needle and the long sheath are preliminarily judged by the length of the handle of the puncture needle left outside the long sheath; when being exposed outside the inner sheath by not more than 1 mm, the atrial septal puncture needle can be displayed on the three-dimensional system to accurately judge the absolute position and the relative position of the needle and the sheath.

Preferably, it is judged whether the atrial septal puncture needle enters the left atrium by that the atrial septal puncture needle penetrates through the right atrium into the left atrium by not greater than 5 mm in a three-dimensional reconstruction model.

Preferably, the guidewire and the long sheath are delivered into the left atrium after the atrial septal puncture; after the atrial septal puncture needle is fixed, the inner sheath is stably delivered together into the left atrium by 4-6 mm, and the atrial septal puncture needle is withdrawn and exchanged into the guidewire, with the electrode tail wire connected; and the guidewire is visible under the three-dimensional mapping system, and now the guidewire should be seen in the region of the left atrium.

Preferably, according to an embodiment of the present invention, the guidewire comprises an insulating portion and conductive portions provided at both ends thereof.

The insulating portion and the conductive portion are of an integral structure or separate structures.

When the insulating portion and the conductive portion are of an integral structure, the insulating portion is coated with an insulating coating, and the conductive portions at both ends are exposed.

When the insulating portion and the conductive portion are separate structures, the insulating portion is a sleeve made of an insulating material, and the conductive portions are provided at both ends of the sleeve.

A wire is provided between the conductive portions at both ends.

The insulating portion is a sleeve made of an insulating material, the entire body inside the sleeve is provided with a conductive portion, and the conductive portion respectively extends a portion out of both ends of the sleeve.

When in use, one end of the conductive portion is connected to a tail wire, and the other end displays the position of the guidewire in the three-dimensional system in real time.

The tail end of the puncture needle is also connected with an intracardiac pressure transducer.

In a preferred embodiment of the present invention, the three-dimensional atrial septal puncture method is operated entirely under a three-dimensional interface without the need for X-rays and contrast agents. The accuracy and success rate of atrial septal puncture can be improved, and safety is guaranteed completely. Moreover, the atrial septal puncture is performed by analyzing the structure and the potential of the right atrial septal face, which is completely different from the traditional method for analyzing the structure of the left atrial septal face, and has greatly changed the idea of the current atrial septal puncture technology.

BRIEF DESCRIPTION OF THE DRAWINGS

FIG. 1 is a flow chart of a three-dimensional atrial septal puncture method of the present invention;

FIG. 2a shows projected positions of the tricuspid annulus (T), mitral annulus (M), aortic annulus (A), and pulmonary artery annulus (P) on the body surface;

DETAILED DESCRIPTION OF THE INVENTION

Hereinafter, technical solutions of the present invention will be described in further detail by means of implementation with reference to the accompanying drawings, but the present invention is not limited to the following embodiments.

FIG. 1 is a flow chart of a three-dimensional atrial septal puncture method of the present invention, comprising 12 steps. Step 1 is the preparatory work before operation, with the structure of heart and blood vessels known in advance by means of imaging. The step 1 includes analyzing the heart and the blood vessel structure by using an existing imaging method to know whether the heart and the blood vessel structure have variations, and mainly analyzing the spatial relationship of the left atrium, the right atrium, the superior vena cava, the inferior vena cava, the coronary sinus and the ascending aorta, and the like, such as whether the oval foramen is defective and the defect degree, whether the superior vena cava and the inferior vena cava are normal in shape, the adjacent degree between the left atrium and the right atrium, the width of the ascending aorta, and whether there is congenital heart or vascular malformation.

Figure 2B:
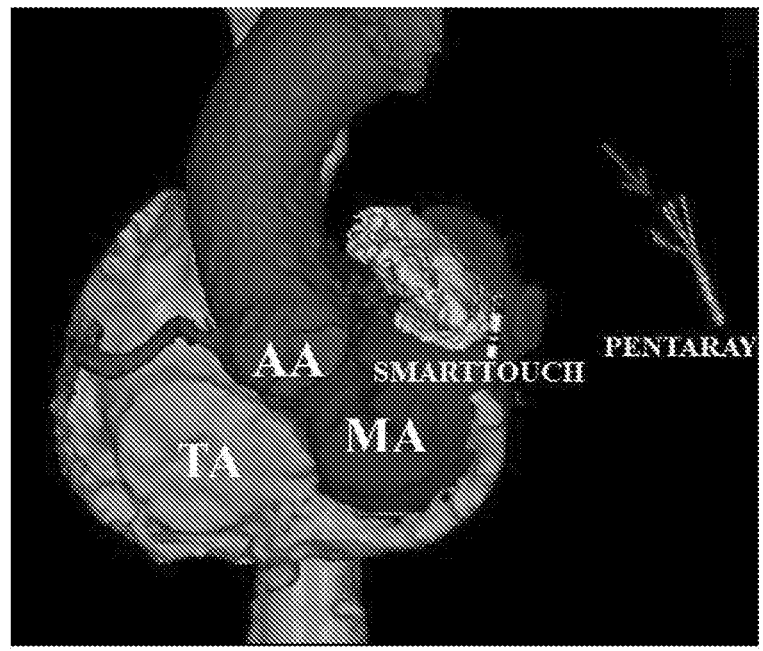
FIG. 2b is a three-dimensional reconstruction of the left atrium, right atrium and ascending aorta.

Step 2 includes positioning the heart by a three-dimensional projection, positioning the heart from the body surface by a three-dimensional projection positioning method, and guiding an interventional instrument into a cardiac chamber in three dimensions. FIG. 2a shows projected positions of the tricuspid annulus (T), mitral annulus (M), aortic annulus (A), and pulmonary artery annulus (P) on the body surface. The arrow indicates the median sternal fourth intercostal or papillary height corresponding approximately to the intracardiac tricuspid annulus position. FIG. 2b is a three-dimensional reconstruction of the left atrium, right atrium and ascending aorta with the left arrow being a pressure sensing catheter placed at the above-described locations on the body surface and the right arrow being a multilevel catheter delivered into the left atrium. Atrial potentials can be recorded at this time, suggesting that the CT images which have been in the atrium, in vivo, in vitro and reconstructed in three-dimensional reconstruction substantially correspond in the height of a longitudinal section.

According to an embodiment of the invention, the step 2 can be operated by the following method: taking the CARTO 3 system of Biosense Webster as an example, a pressure sensing catheter, such as a SMARTTOUCH catheter, is placed in the precordial region. The catheter contacts the body surface of the patient as much as possible, different positions of the body surface roughly correspond to different regions in the heart, and the spatial position of the heart in a three-dimensional system can be preliminarily judged and marked. An annular electrode catheter, such as a LASSO-NAV or PENTARAY electrode catheter, is then delivered into the heart chamber and may also be operated with a pressure sensing catheter, the general position of which in the heart chamber may be initially determined in the three-dimensional system by comparing locating points on the body surface.

Figure 3:
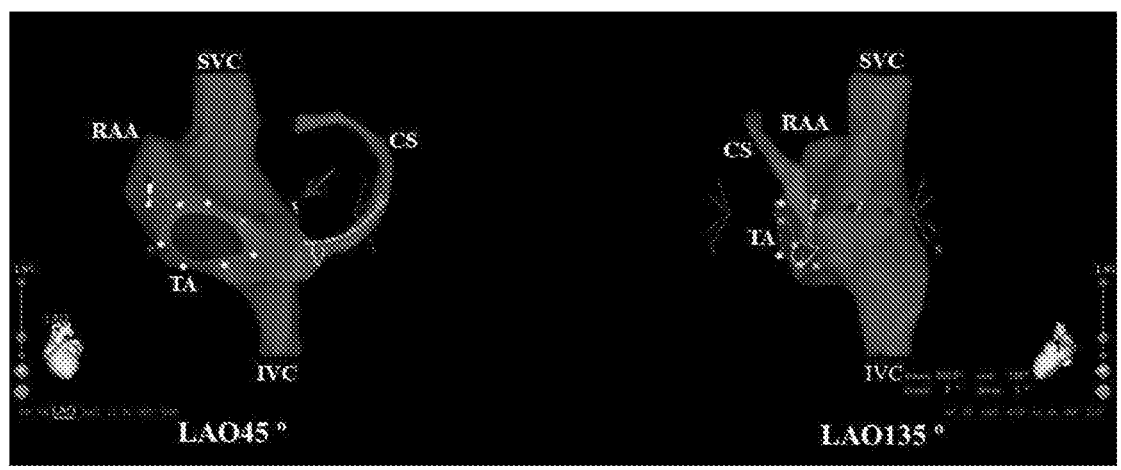
FIG. 3 shows a three-dimensional reconstruction of the right atrium under the guidance of the CARTO3 system.

Step 3 includes three-dimensionally reconstructing a heart structure, constructing a right atrium three-dimensional model, puncturing a right femoral vein, and delivering a catheter with a magnetic positioning device into the right femoral vein; and reconstructing a three-dimensional anatomical structure of the right atrium. FIG. 3 shows a three-dimensional reconstruction of the right atrium guided by the CARTO3 system, in which the right atrial septal face and the coronary sinus region are important. The arrow shows a puncture site, with an upper and lower height, i.e. the longitudinal section, being approximately at the level of the His bundle of the right atrium; and with an anterior-posterior position, i.e. the cross section, being approximately at the last one third of the right atrial septal face. In the patent, SVC is the superior vena cava, IVC is the inferior vena cava, RAA is the right atrial appendage, CS is the coronary sinus, TA is the tricuspid annulus, and LAO is the left anterior oblique position.

According to an embodiment of the invention, the following operation method can be adopted in the step 3: this embodiment is exemplified by a SWARTS L1-type 8.5F fixed curved long sheath and associated guidewire from St. Jude Inc. The right femoral vein is punctured, and a long guidewire is delivered; if no resistance exists, the long guidewire can be delivered into the blood vessel by 50-60 cm, and guided to the right atrium; the long sheath and guidewire are withdrawn and exchanged into a SMART-TOUCH catheter or LASSONAV catheter or PENTARAY catheter from Johnson & Johnson Electrophysiology, Inc. If the SMARTTOUCH catheter is used, the pressure display should be started, with the pressure not exceeding 20 g. Alternatively, the long sheath may be delivered directly into a catheter having a magnetic positioning device without using a guidewire to guide the long sheath. For example, the CARTO3 system of Johnson & Johnson Electrophysiology, Inc. can be used to first perform respiratory gating followed by reconstruction of the right atrial three-dimensional anatomical structure with a SMARTTOUCH catheter, a LASSO NAV catheter, or a PENTARAY catheter.

Figure 4:
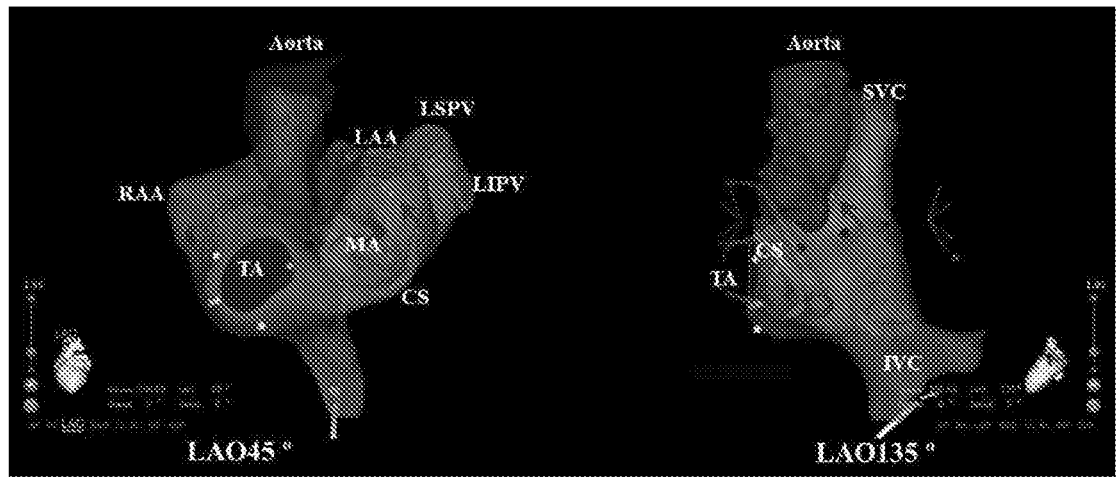
FIG. 4 shows the CT or MRI image data that can be reconstructed and fused by a CARTO3 three-dimensional system.

Step 4 includes performing image fusion analysis, and carrying out three-dimensional reconstruction and image fusion on the CT or MRI performed before the operation. FIG. 4 shows the CT or MRI image data that can be reconstructed and fused by using a CARTO3 three-dimensional system, with the arrow showing visualized atrial septal needles. LAA is the left atrial appendage, MA is the mitral annulus, LSPV is the left superior pulmonary vein, LIPV is the left inferior pulmonary vein, and Aorta is the aorta. The specific operation method of the step 4 includes the following steps: the structural details of the atrial septum and the adjacent relationship among the left atrium, the right atrium and the aorta will be clearer when the alignment points are selected from the coronary sinus ostium, the tricuspid annulus and the orifice of superior vena cava. The pre-operative CT or MRI image data can be reconstructed by the CARTO3 three-dimensional system; the reconstructed structure, such as the right atrium, can be placed in a three-dimensional window to serve as a reference during modeling; and finally image fusion can be carried out, so that the right atrium three-dimensional anatomical structure can be constructed more accurately. The step 4 may also be direct making of the atrial septal puncture point without image fusion analysis.

Step 5 includes marking the atrial septal puncture point, as shown in FIG. 3. The right atrial septal side is mainly analyzed to mark the puncture site. The atrial septal puncture site may be marked by using the following methods: after the three-dimensional anatomical structure of the right atrium is reconstructed, the spatial anatomical positions of the tricuspid annulus, the His bundle, the coronary sinus, the superior vena cava, the inferior vena cava and the like are marked, the septum surface is mainly constructed, and the right-to-left bulge can be recorded in the fossa ovalis area at most times. Preferably, the coronary sinus is marked at a distal end by using a catheter with a pressure sensor. For example, the SMARTTOUCH catheter may be used at pressures of not more than 20 g. Most atrial septal puncture points located in the fossa ovalis are generally at a height level of the His bundle in the longitudinal section, not more than 5 mm above or below the level; most of the atrial septal puncture points are located in a bulge region at a position of last two fifths to one quarter of the septum in the transverse section; and the potential characteristics include the potential measured at the center of the fossa ovalis is significantly less than that at the periphery of the fossa ovalis.

Figure 5A:
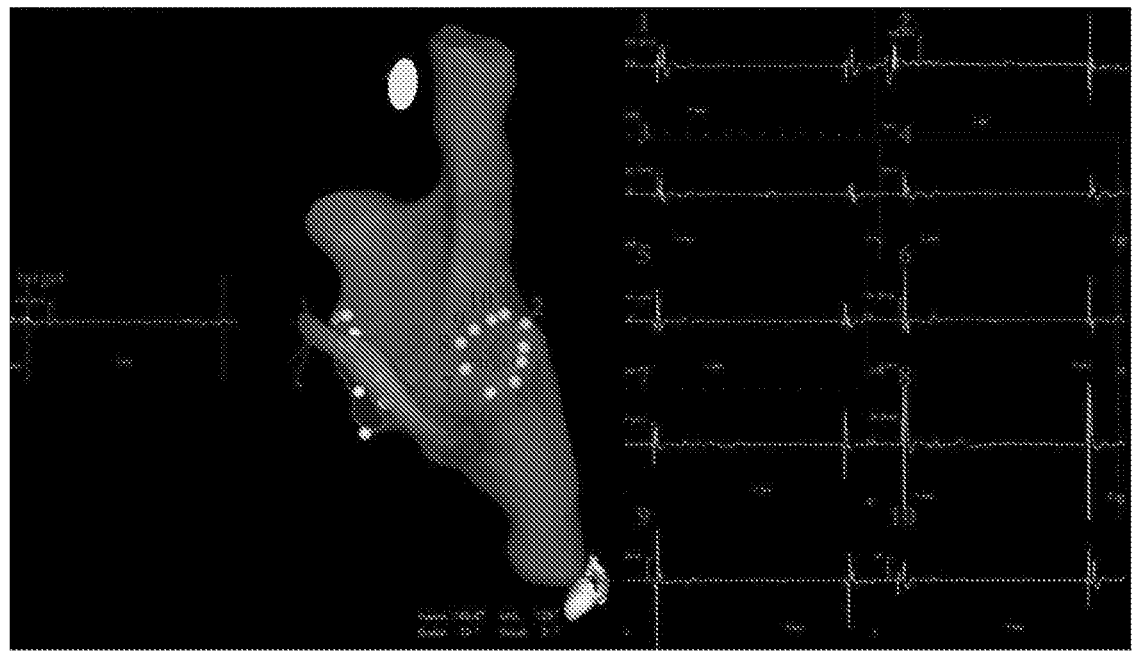
FIG. 5a is a potential diagram of the fossa ovalis under sinus rhythm.
Figure 5B:
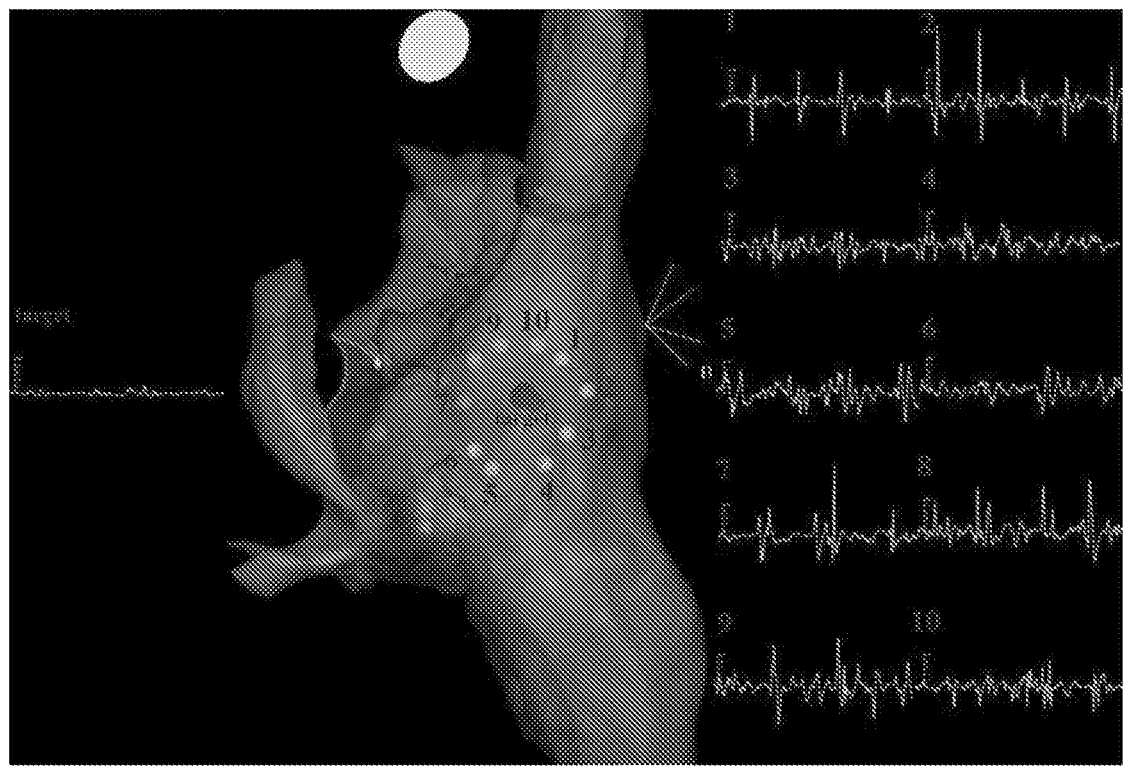
FIG. 5b is a potential diagram of the fossa ovalis under the atrial fibrillation rhythm.

According to another embodiment of the present invention, the atrial septal puncture point may also be marked by marking the atrial septal puncture point after the fossa ovalis is positioned by potential mapping. FIG. 5a is a potential diagram of the fossa ovalis under the sinus rhythm; under the sinus rhythm, the fossa ovalis position is analyzed structurally, and multi-point mapping (e.g., points numbered 1-10 on the image) is performed at the position of the fossa ovalis, the points being local potentials at the periphery of the fossa ovalis after three-dimensional electroanatomical reconstruction of the right atrium; and potential characteristics of a point in the middle of the points (marked with a target) is then marked, and if the point is a fossa ovalis potential, the amplitude of potential is obviously less than that of the former, the point being the best puncture point. FIG. 5b is a potential diagram of the fossa ovalis potential under the atrial fibrillation rhythm; under the atrial fibrillation rhythm, the fossa ovalis position is analyzed structurally, and multi-point mapping (e.g., points numbered 1-10 on the image) is performed at the position of the fossa ovalis, the points being local potentials at the periphery of the fossa ovalis after three-dimensional electroanatomical reconstruction of the right atrium; and potential characteristics of a point in the middle of the points (marked with a target) is then marked, and if the point is a fossa ovalis potential, the amplitude and frequency of potential is obviously less than that of the former, the point being the best puncture point.

The atrial septal puncture point can be marked by using the above two methods or either of the two methods.

Figure 6A:
FIGS. 6a and 6b visualize a guidewire in the superior vena cava, within a white circle.
Figure 6B:
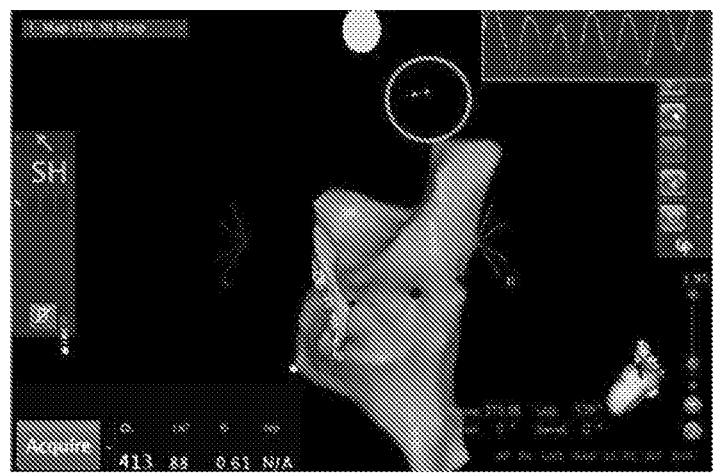
Figure 6C:
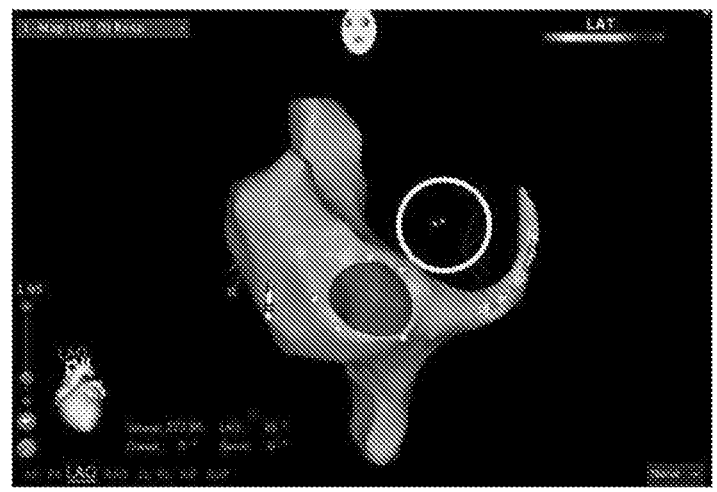
FIGS. 6c and 6d visualize an atrial septal puncture needle through the septum into the left atrium, within a white circle.
Figure 6D:
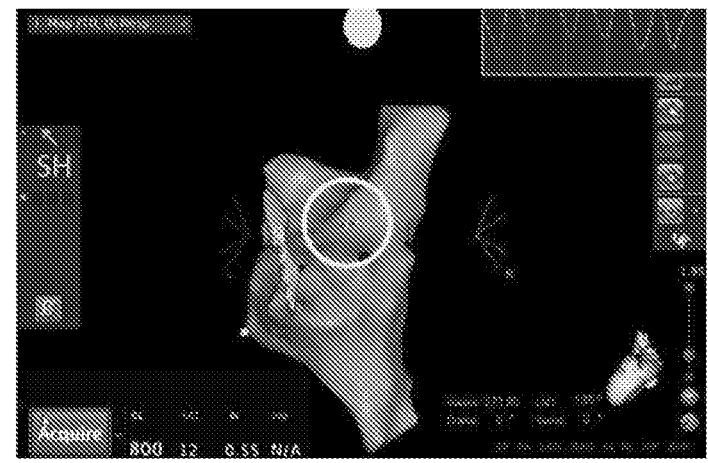
Figure 7:
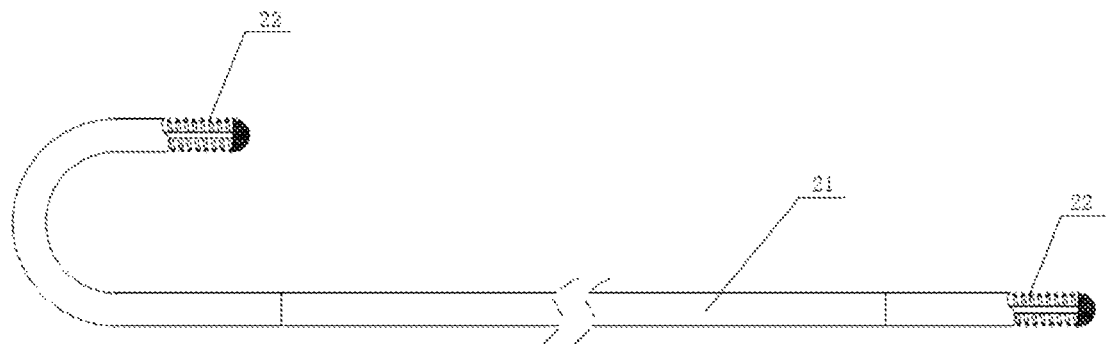
FIG. 7 is a structurally schematic view of the guidewire.

Step 6 is visualization of the guidewire and atrial septal puncture needle. FIGS. 6a and 6b visualize a guidewire in the superior vena cava, within a white circle. FIGS. 6c and 6d visualize an atrial septal puncture through the septum into the left atrium, within a white circle. FIG. 7 is a structurally schematic view of the guidewire; and the guidewire 20 includes an insulating portion 21 and conductive portions 22 provided at both ends thereof, as shown in FIG. 7. The conductive portion 21 is made of a conductive material, such as a spring tube or other suitable structure, and has a length of 3-6 mm. The insulating portion may be an insulating coating or a sleeve made of an insulating material. The insulating portion 21 and the conductive portion 22 may be of an integral structure or separate structures. When the insulating portion 21 and the conductive portion 22 are of an integral structure, the insulating portion 21 may be coated with an insulating coating, and the conductive portions 22 at both ends are exposed. When the insulating portion 21 and the conductive portion 22 are separate structures, the insulating portion 21 can be a sleeve made of an insulating material, and the conductive portion 22 can be only provided at both ends of the sleeve; it is also possible that the entire body inside the sleeve is provided with a conductive portion, and the conductive portion respectively extends a portion out of both ends of the sleeve. When the conductive portions 22 are provided only at the both ends of the sleeve, a wire is provided between the conductive portions at the both ends; and the wire may be a conventional wire, a core wire or other suitable structure for conducting between the conductive portions at the both ends. In use, one end of the conductive portion 21 can be connected to a tail wire, and the other end can display the position of the guidewire in a three-dimensional system in real time. The guidewires described in the present invention can each preferably be a guidewire having the structure shown in FIG. 7, or other guidewires having a suitable structure and good electrical conductivity.

The specific operation of the step 6 is as follows: firstly, parameter setting of the three-dimensional system and tail wire connection of an operating device are carried out. The operating device is respectively connected with a pressure sensor tail wire and an electrode tail wire. Any good conductor, such as a guidewire or puncture needle, may be defined in the system as a bipolar mapping catheter and connected to the three-dimensional mapping system via a bipolar connecting tail wire. The tail end of the puncture needle can also be connected with an intracardiac pressure transducer.

According to an embodiment of the present invention, an operator can customize a bipolar electrode in the system according to the settings of the CARTO3 system of Johnson & Johnson Electrophysiology, Inc. When a conductor is connected to the CARTO3 system via a bipolar electrode tail wire, the system, upon receiving an electrical signal, marks the guidewire or puncture needle as a bipolar electrode and displays its real-time position in a three-dimensional window.

Figure 8:
FIG. 8 shows a distal end of the guidewire positioned in the superior vena cava.
Figure 9:
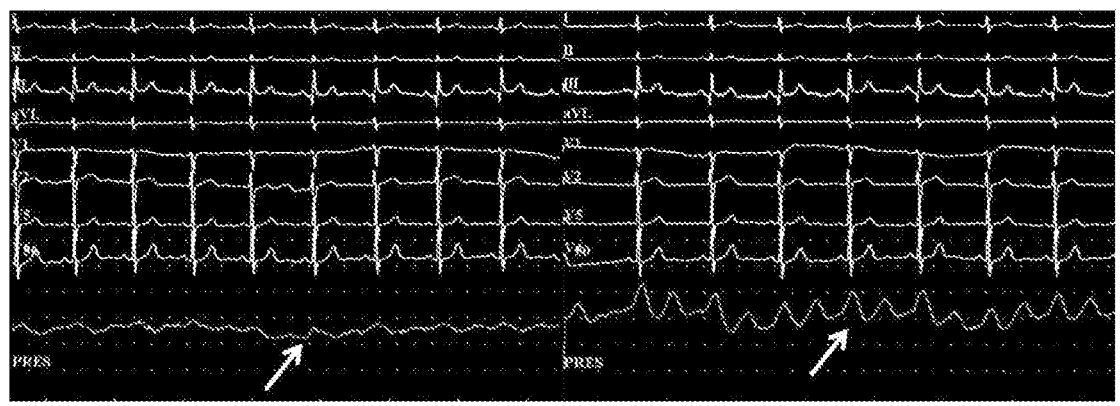
FIG. 9 shows the right atrial pressure curve at the left portion, and shows the left atrial pressure curve at the right portion.

Step 7 includes delivering the long sheath into the superior vena cava, visualizing the guidewire and positioning the long sheath by using a three-dimensional mapping system. FIG. 8 shows that the distal end of the guidewire has been located in the superior vena cava. As indicated by the arrow, when the distal end of the guidewire extends out of the inner sheath by not more than 1-2 mm, the distal end of the guidewire can be displayed in the three-dimensional system. The specific operation method of the step 7 includes delivering and guiding the long sheath to the right atrium, connecting the guidewire to the three-dimensional system to display the position of the distal end of the guidewire, judging the spatial position of the head end of the long sheath according to the position, withdrawing the inner sheath and the guidewire, and exchanging the inner sheath and the guidewire into a catheter with a magnetic positioning device. In accordance with an embodiment of the present invention, it is exemplified by a SWARTS L1-type 8.5F fixed curved long sheath and associated guidewire from St. Jude Inc. to deliver a long guidewire, and a bipolar electrode tail is connected to the tail end of the guidewire so as to display the guidewire. Preferably, when the guidewire exits the sheath by not greater than 1-2 mm, the true position of the guidewire is reflected in the three-dimensional system, and the spatial position of the SWARTS sheath can be known. This is the position of the sheath if the guidewire is withdrawn into the sheath so that the guidewire disappears in the three-dimensional system. The inner sheath and guidewire are withdrawn and exchanged into a SMART-TOUCH catheter, a LASSO NAV catheter or a PENTARAY catheter from Johnson & Johnson Electrophysiology, Inc. If the SMARTTOUCH catheter is used, the pressure display should be started. In the step, the guidewire can be not used for guiding the long sheath, and a catheter with a magnetic positioning device can be directly used for guiding the long sheath; and the three-dimensional system can prompt when the catheter goes out of the long sheath or is in the long sheath, so that the position of the head end of the long sheath can be judged.

Step 8 includes performing the atrial septal puncture under the guidance of a three-dimensional system, wherein the operation method includes the following steps: a guidewire and long sheath are first delivered into the superior vena cava. The long sheath is delivered into the superior vena cava by using a catheter with a magnetic positioning device and then exchanged into an inner sheath with the guidewire. The guidewire always remains outside the inner sheath, and when the distal end of the guidewire extends out of the inner sheath by not greater than 1-2 mm, the head end of the guidewire can be displayed in the three-dimensional system. Here, the distal end of the guidewire may be slightly exposed to the sheath, showing the right atrial septal face at a left anterior oblique angle of 45 degrees and a left anterior oblique angle of 135 degrees respectively in the three-dimensional system. The guidewire is exchanged into the atrial septal puncture needle, and the relative position of the atrial septal puncture needle and the long sheath is judged by the length of the handle of the puncture needle left outside the long sheath, so as to determine the position of the atrial septal puncture needle. The atrial septal puncture needle is visualized by using the three-dimensional mapping system.

When the needle tip out of the sheath is not greater than 1 mm, the needle can be displayed on the three-dimensional mapping system to judge the position of the atrial septal puncture needle in the heart and blood vessels. The atrial septal puncture needle handle indicator and the long sheath is pointed in the direction of 3 to 4 o'clock and pulled down in the meantime, and the movement of the puncture needle can be seen in the three-dimensional system. When the atrial septal puncture needle slides to a marked puncture point, namely the position of the oval foramen of the atrial septum, it generally tends to cause an empty feeling; the position of the atrial septal puncture needle is properly adjusted to accurately reach the marked site, now we can try to pass through the septum; and it generally tends to cause a feeling of puncturing through when passing through the septum. At this time, the atrial septal puncture needle can be clearly seen in the direction to puncture through the right atrial structure into the left atrium in the three-dimensional system. If the images are fused, the three-dimensional spatial relationship between the puncture needle and structures of the left atrium, the right atrium, the aorta and the like can be clearly seen. It is noted that the aorta should be avoided. And if it fails, the above process is repeated to carry out the next try for a pass-through.

Step 9 is an analysis for the pressure difference between the left atrium and the right atrium, with the right atrial pressure curve shown in the left portion of FIG. 8 and the left atrial pressure curve shown in the right portion of FIG. 8, showing a significant increase in pressure after entry of the puncture needle into the left atrium. It can be judged whether the atrial septal puncture needle enters the left atrium by drawing return blood and observing the change of the return blood color and speed and the pressure rise.

Figure 10:
FIG. 10 shows that after successful puncture, the puncture needle shown by the arrow enters the left atrium by not more than 1 cm.

Step 10 is a judgment of whether the puncture is successful. FIG. 10 shows the atrial septal puncture needle shown by the arrow entering the left atrium after a successful puncture. It can be judged whether the puncture needle enters the left atrium by the following method: it generally tends to cause a feeling of puncturing through when passing through the septum; in the three-dimensional reconstruction model, it can be clearly seen that the atrial septal puncture needle punctures through the right atrium to enter the left atrium by not more than 5 mm; if the images are fused, it will be more visualized; the blood drawn is left heart blood with bright colors; and when the intracardiac pressure transducer is connected, the process that the pressure rises from the right atrium to the left atrium in most cases can be seen. If the puncture is still unsuccessful, the above process is repeated.

Figure 11:
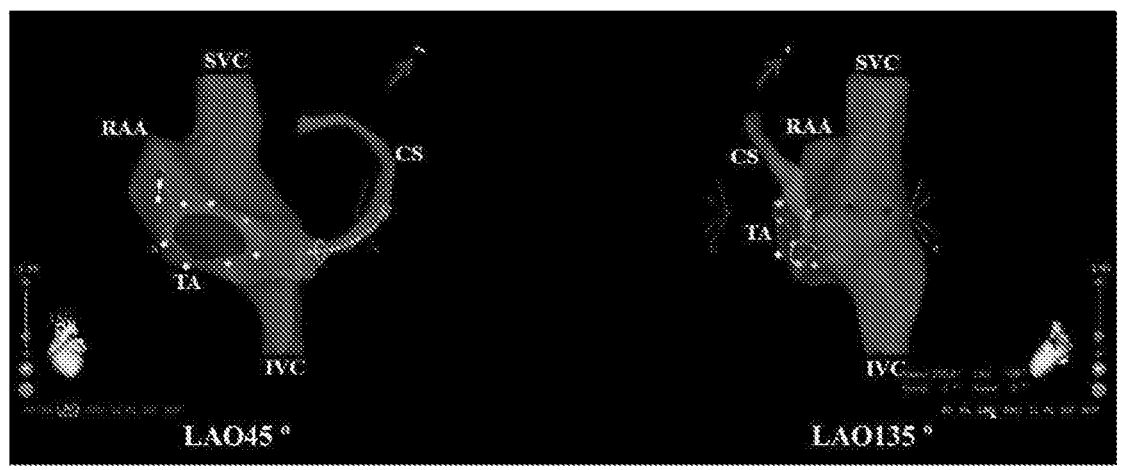
FIG. 11 shows the guidewire entering the left atrium at a position slightly distal from the atrial septal puncture point.

Step 11 includes inserting the guidewire into the left atrium after the atrial septal puncture. Step 12 includes guiding the long sheath into the left atrium after the atrial septal puncture. FIG. 11 shows the guidewire entering the left atrium, and the figure shows the conditions inside the left superior pulmonary vein and can be more clearly shown if there is image fusion. Since the catheter previously attempts to construct the distal end of the coronary sinus, the three-dimensional system is able to correctly display the position of the guidewire.

After the atrial septal puncture needle is fixed, the inner sheath is stably delivered together in the direction of the left atrium by 4-6 mm, preferably about 5 mm or 5 mm or more; the atrial septal puncture needle is withdrawn and exchanged into a guidewire, with the electrode tail wire connected; and the guidewire is visible under the three-dimensional mapping system, and now the guidewire should be seen in the region of the left atrium. The guidewire is delivered suitably farther, e.g., proximal to the left superior pulmonary vein, and should be found near the distal end of the coronary sinus in the three-dimensional system. If there is an image fused with the pre-reconstructed left atrium, the procedure is clearer; and if a preferred guidewire 20 is used, it is more accurate. The inner sheath and the outer sheath are delivered into the left atrium along the guidewire by not greater than 1 cm, and it mostly causes a feeling of puncturing through. The inner sheath and the guidewire are withdrawn, and delivered into a mapping catheter or an ablation catheter to the vicinity of the mitral annulus under the guidance of a three-dimensional mapping system; characteristic electricity on the mitral annulus can be seen at the moment, with both A and V being available, and whether the puncture position is ideal can be preliminarily judged now.

According to the three-dimensional atrial septal puncture method provided by the invention, zero-ray atrial septal puncture can be realized without depending on ultrasound; and the method is even superior to the ultrasound method due to the fact that the oval fossa potential analysis technology is added, so that the whole-course zero-ray of most radiofrequency ablation is realized, and the heart interventional operation without an X-ray machine is possible. Due to the fact that three-dimensional navigation equipment is commonly provided in a clinical cardiac radiofrequency surgery at present, the equipment can be fully utilized in the method provided by the invention, thereby not only saving the huge cost of using ultrasound, but also greatly improving the accuracy and safety of puncture under the guidance of X rays.

The embodiments of the present invention are not limited to the above-described embodiments, and various changes and modifications in form and detail by those skilled in the art may be made without departing from the spirit and scope of the present invention, which is considered as falling within the scope of the present invention.

The invention claimed is:

1. Three-dimensional atrial septal puncture method, characterized by comprising the steps of:
   positioning the heart from a body surface by a three-dimensional projection positioning method, displaying an interventional instrument in a three-dimensional system and guiding the same into a cardiac chamber; constructing a right atrium three-dimensional model by delivering a catheter with a positioning device to the right atrium; mainly constructing a right atrial septal side, and analyzing the position and/or potential characteristics of the fossa ovalis and marking the fossa ovalis as a puncture site;
   setting parameters of the three-dimensional system, connecting a puncture operation device with a corresponding electrode tail wire and to the three-dimensional system, and displaying a guidewire or a puncture needle in the three-dimensional system in real time;
   delivering a long sheath into the superior vena cava, and positioning the long sheath by using the three-dimensional system;
   performing the atrial septal puncture at an atrial septal marker site by the delivered atrial septal puncture needle under the guidance of the three-dimensional system;
   connecting a tail end of the puncture needle with a pressure sensor tail wire, and judging whether the puncture is successful by analyzing the pressure difference between the left atrium and the right atrium; and
   sequentially delivering the guidewire and the long sheath into the left atrium after a successful atrial septal puncture.

2. The three-dimensional atrial septal puncture method according to claim 1, characterized in that the reconstruction of the three-dimensional system is followed by image fusion analysis.

3. The three-dimensional atrial septal puncture method according to claim 2, characterized in that after the reconstruction of the three-dimensional system, the fossa ovalis is positioned by potential mapping to mark an atrial septal puncture point.

4. The three-dimensional atrial septal puncture method according to claim 2, characterized in that when the atrial septal puncture site is marked, the coronary sinus is marked at a distal end by using a catheter with a pressure sensor.

5. The three-dimensional atrial septal puncture method according to claim 1, characterized in that the atrial septal puncture point located in the fossa ovalis is at a height level of the His bundle in the longitudinal section, not more than 5 mm above or below the level, and is located in a bulge region at a position of last two fifths to one quarter of the septum in the transverse section; preferably, the potential measured at the center of the fossa ovalis is significantly less than the potential at the periphery of the fossa ovalis.

6. The three-dimensional atrial septal puncture method according to claim 1, characterized in that the guidewire or atrial septal puncture needle is defined as a mapping catheter, and the mapping catheter is connected into the three-dimensional system by connecting a tail wire; and preferably, the tail end of the atrial septal puncture needle is also connected to an intracardiac pressure transducer.

7. The three-dimensional atrial septal puncture method according to claim 1, characterized in that the long sheath is delivered into the superior vena cava by using a catheter with a magnetic positioning device and then exchanged into an inner sheath and a guidewire; the guidewire always remains outside the inner sheath, and the length of the distal end of the guidewire extending out of the inner sheath is not greater than 1-2 mm, so that the head end of the guidewire can be displayed in the three-dimensional system.

8. The three-dimensional atrial septal puncture method according to claim 1, characterized in that the distal end of the guidewire is delivered into the superior vena cava directly by means of slight or even no exposure to the long sheath; the right atrial septal face is displayed at a left anterior oblique angle of 45 degrees and a left anterior oblique angle of 135 degrees respectively in the three-dimensional system; the guidewire is exchanged into the atrial septal puncture needle, the relative positions of the puncture needle and the long sheath are preliminarily judged by the length of the handle of the puncture needle left outside the long sheath, and when the length of the distal end of the atrial septal puncture needle extending out of the inner sheath is not greater than 1 mm, the atrial septal puncture needle can be clearly displayed in the three-dimensional system.

9. The three-dimensional atrial septal puncture method according to claim 1, characterized in that it is judged whether the atrial septal puncture needle enters the left atrium by that the atrial septal puncture needle penetrates through the right atrium into the left atrium by not greater than 5 mm in a three-dimensional reconstruction model.

10. The three-dimensional atrial septal puncture method according to claim 1, characterized in that the guidewire and the long sheath are delivered into the left atrium after the atrial septal puncture: after the atrial septal puncture needle is fixed, the inner sheath is stably delivered together into the left atrium by 4-6 mm, and the atrial septal puncture needle is withdrawn and exchanged into the guidewire, with the electrode tail wire connected; and the guidewire is visible under the three-dimensional mapping system, and now the guidewire should be seen in the region of the left atrium.

11. The three-dimensional atrial septal puncture method according to claim 1, characterized in that the guidewire comprises an insulating portion and conductive portions provided at both ends thereof; and preferably, the insulating portion and the conductive portion are of an integral structure or separate structures.

12. The three-dimensional atrial septal puncture method according to claim 11, characterized in that when the insulating portion and the conductive portion are of an integral structure, the insulating portion is coated with an insulating coating and the conductive portions at both ends are exposed.

13. The three-dimensional atrial septal puncture method according to claim 11, characterized in that when the insulating portion and the conductive portion are separate structures, the insulating portion is a sleeve made of an insulating material, and the conductive portions are provided at both ends of the sleeve; and preferably, a wire is provided between the conductive portions at both ends.

14. The three-dimensional atrial septal puncture method according to claim 11, characterized in that the insulating portion is a sleeve made of an insulating material, the entire body inside the sleeve is provided with a conductive portion, and the conductive portion respectively extends a portion out of both ends of the sleeve; and preferably, when in use, one end of the conductive portion is connected to a tail wire, and the other end displays the position of the guidewire in the three-dimensional system in real time.

* * * * *